United States Patent
Dupont et al.

(10) Patent No.: US 6,897,189 B2
(45) Date of Patent: May 24, 2005

(54) ANTI-WRINKLE SILICONE POLYSACCHARIDE COMPOUNDS AND COMPOSITIONS COMPRISING SAID COMPOUNDS

(75) Inventors: Jeffrey Scott Dupont, Cincinnati, OH (US); Rajan Keshav Panandiker, West Chester, OH (US); Jiping Wang, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 316 days.

(21) Appl. No.: 10/309,982

(22) Filed: Dec. 4, 2002

(65) Prior Publication Data

US 2003/0144169 A1 Jul. 31, 2003

Related U.S. Application Data

(60) Provisional application No. 60/337,941, filed on Dec. 7, 2001.

(51) Int. Cl.[7] .............................. C11D 3/22; C11D 9/36
(52) U.S. Cl. ........................ 510/287; 510/276; 510/466; 510/470; 536/45; 536/55.1; 536/102; 536/123.1
(58) Field of Search .................... 536/45, 55.1, 102, 536/123.1; 510/276, 287, 466, 470

(56) References Cited

U.S. PATENT DOCUMENTS

| | | | | |
|---|---|---|---|---|
| 5,059,686 A | * | 10/1991 | Sau | ............................ 536/114 |
| 6,703,027 B2 | * | 3/2004 | Kurosawa et al. | .......... 424/401 |
| 2001/0003925 A1 | | 6/2001 | Swan | |

FOREIGN PATENT DOCUMENTS

| EP | 0 385 396 A1 | 9/1990 |
|---|---|---|
| WO | WO 99/14245 A1 | 3/1999 |

* cited by examiner

*Primary Examiner*—Charles Boyer
(74) *Attorney, Agent, or Firm*—Brian M. Bolam; Brahm J. Corstanje; Kim William Zerby

(57) ABSTRACT

The present invention relates to compounds, and laundry compositions comprising said compounds, which are capable of providing enhanced anti-wrinkle benefits to cellulosic fiber containing fabric, said compounds having the formula:

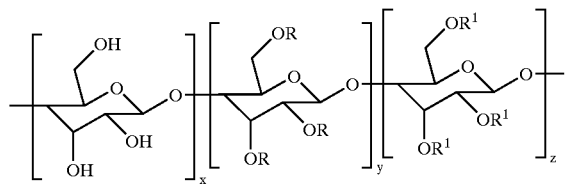

wherein each R unit is independently a siloxane units having the formula:

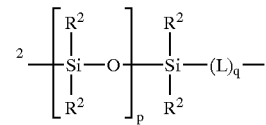

wherein each $R^2$ is independently a $C_1$–$C_{22}$ linear or branched, substituted or unsubstituted hydrocarbyl moiety; the index p is from 0 to about 50; L is a linking group; the index q is 0 or 1; $R^1$ units are fabric substantive units having the formula:

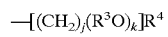

wherein $R^3$ is $C_2$–$C_{12}$ linear or branched alkylene; $R^4$ is hydrogen, an anionic unit, and mixtures thereof; the index j is from 0 to about 25; the index k is from 0 to about 50; the sum of the indices x+y+z=n wherein n has an average value of from 5 to about 6000;.

23 Claims, No Drawings

ANTI-WRINKLE SILICONE POLYSACCHARIDE COMPOUNDS AND COMPOSITIONS COMPRISING SAID COMPOUNDS

CROSS REFERENCE TO RELATED APPLICATIONS

This application claims priority under 35 U.S.C. § 119(e) to U.S. Provisional Application Ser. No. 60/337,941, filed Dec. 7, 2001.

FIELD OF THE INVENTION

The present invention relates to polysaccharide oligomers and/or polymers that are modified to provide compounds having an anti-wrinkle benefit to garments and textiles. The present invention further relates to laundry detergent compositions that comprise said anti-wrinkle benefit compounds.

BACKGROUND OF THE INVENTION

Fabric, primarily cellulose comprising fabric, inter alia, cotton, has a propensity to wrinkle when laundered. Cotton fabric, which secondary structure is determined by the hydrogen bonds formed between proximal saccharide residues, becomes wrinkled when said hydrogen bonds are formed between units that are further away from one another than the original bonds. Wrinkling can occur under a number of circumstances including loss of nascent water from fabric while the fabric is not spread flat or if the fabric is mechanically bent or folded.

Manufacturers of cellulose comprising fabric have long sought to abate the propensity of this type of fabric to wrinkle. One means has been to treat the fabric during the manufacture stage with crosslinking agents that provide a rigid fiber matrix, for example, permanent press treatments involving formaldehyde or other reactive crosslinking agents.

Treatment of fabric, however, can relate to the loss of properties which are desired, inter alia, strength, breathability, softness. There is therefore a long felt need for a means of providing anti-wrinkle benefits to fabric which does not modify the surface of the fabric in a manner which detracts from the fabric qualities.

SUMMARY OF THE INVENTION

The present invention meets the aforementioned needs in that it has been surprisingly discovered that polysaccharide oligomers and polymers that have been modified with siloxane units and a anionic, nonionic, cationic or zwitterionic unit provides anti-wrinkle benefits.

The first aspect of the present invention relates to compounds which are capable of providing enhanced anti-wrinkle benefits to cellulosic fiber containing fabric, said compounds having the formula:

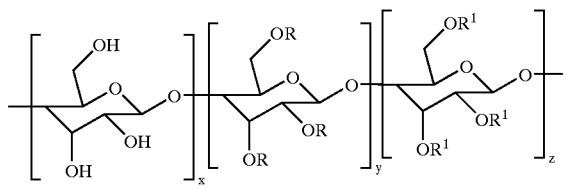

wherein each R units are independently siloxane units having the formula:

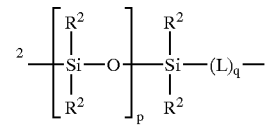

wherein each $R^2$ is independently a $C_1$–$C_{22}$ linear or branched, substituted or unsubstituted hydrocarbyl moiety; the index p is from 0 to about 50; L is a linking group; the index q is 0 or 1; each $R^1$ unit is independently fabric substantive units having the formula:

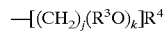

wherein $R^3$ is $C_2$–$C_{12}$ linear or branched alkylene; $R^4$ is hydrogen, an anionic unit, and mixtures thereof; the index j is from 0 to about 25; the index k is from 0 to about 50; the sum of the indices x+y+z=n wherein n has an average value of from 5 to about 6000.

The present invention further relates to laundry detergent compositions comprising the anti-wrinkle compounds of the present invention.

Another aspect of the present invention relates to methods for providing enhanced anti-wrinkle benefits to fabric.

These and other objects, features, and advantages will become apparent to those of ordinary skill in the art from a reading of the following detailed description and the appended claims. All percentages, ratios and proportions herein are by weight, unless otherwise specified.

All temperatures are in degrees Celsius (° C.) unless otherwise specified. All documents cited are in relevant part, incorporated herein by reference.

DETAILED DESCRIPTION OF THE INVENTION

The present invention relates to modified polysaccharides that provide anti-wrinkle benefits to cellulosic fabric, especially cotton fabric. The compositions of the present invention that comprise said modified polysaccharides are capable of enhancing the anti-wrinkle capacity of clothing or other fabric comprising articles of manufacture.

It has now been surprisingly discovered that oligomeric and polymeric polysaccharides can be modified to provide anti-wrinkle benefits. The first modification is the attachment of a siloxane comprising unit which modifies the surface of fabric to provide the anti-wrinkling benefit. The second modification is the attachment of an anionic, nonionic, cationic or zwitterionic unit to the polysaccharide which provides the final compound with increased water dispersibility or increased water solubility depending upon the final molecular weight.

All documents cited are, in relevant part, incorporated herein by reference; the citation of any document is not to be construed as an admission that it is prior art with respect to the present invention.

Definitions

Herein "hydrocarbyl" means any unit which comprises carbon and hydrogen atoms, whether linear, branched, cyclic, acyclic, and regardless of how many of the hydrogen atoms are substituted for with a suitable substituted unit as defined herein below. Non-limiting examples of "hydrocarbyl" units include methyl, benzyl, 6-hydroxyoctanyl, m-chlorophenyl, 2-(N-methylamino)propyl, and the like.

Herein "substituted" means replacement of a hydrogen atom, two hydrogen atoms, or three hydrogen atoms from a carbon atom to form a moiety, or the replacement of hydrogen atoms from adjacent carbon atoms to form a moiety. For example, a substituted unit that requires a single hydrogen atom replacement includes halogen, hydroxyl, and the like. A two hydrogen atom replacement includes carbonyl, oximino, and the like. Three hydrogen replacement includes cyano, and the like. The term substituted is used throughout the present specification to indicate that a moiety, inter alia, aromatic ring, alkyl chain, can have one or more of the hydrogen atoms replaced by a substituent. For example, 4-hydroxyphenyl is a "substituted aromatic carbocyclic ring", and 3-guanidinopropyl is a "substituted $C_3$ alkyl unit."

The following are non-limiting examples of moieties, which can replace hydrogen atoms on carbon to form a "substituted hydrocarbyl" unit:

i) —$NHCOR^{30}$;
ii) —$COR^{30}$;
iii) —$COOR^{30}$;
iv) —$COCH=CH_2$;
v) —$C(=NH)NH_2$;
vi) —$N(R^{30})_2$;
vii) —$NHC_6H_5$;
viii) =$CHC_6H_5$;
ix) —$CON(R^{30})_2$;
x) —$CONHNH_2$;
xi) —NHCN;
xii) —OCN;
xiii) —CN;
xiv) F, Cl, Br, I, and mixtures thereof;
xv) =O;
xvi) —$OR^{30}$;
xvii) —NHCHO;
xviii) —OH;
xix) —$NHN(R^{30})_2$;
xx) =$NR^{30}$;
xxi) =$NOR^{30}$;
xxii) —$NHOR^{30}$;
xxiii) —CNO;
xxiv) —NCS;
xxv) =$C(R^{30})_2$;
xxvi) —$SO_3M$;
xxvii) —$OSO_3M$;
xxviii) —SCN;
xxix) —$P(O)H_2$;
xxx) —$PO_2$;
xxxi) —$P(O)(OH)_2$;
xxxii) —$SO_2NH_2$;
xxxiii) —$SO_2R^{30}$;
xxxiv) —$NO_2$;
xxxv) trihalomethyl having the formula: —$CF_3$, —$CCl_3$, —$CBr_3$;
xxxvi) and mixtures thereof;
wherein $R^{30}$ is hydrogen, $C_1$–$C_{20}$ linear or branched alkyl, $C_6$–$C_{20}$ aryl, $C_7$–$C_{20}$ alkylenearyl, and mixtures thereof; M is hydrogen, or a salt forming cation.

Herein "polysaccharide" means any material comprising a saccharide having the formula described herein below containing the number of units as described herein below. The terms "oligosaccharide", "polysaccharide", "cellulose", "cellulose polymers", "cellulose polysaccharides" and the like are used interchangeably throughout the present specification and are intended to stand for the materials which are suitable backbones for the compounds of the present invention.

Anti-wrinkle Compounds

The anti-wrinkle fabric enhancing compounds of the present invention are polysaccharide oligomers or polymers having the formula:

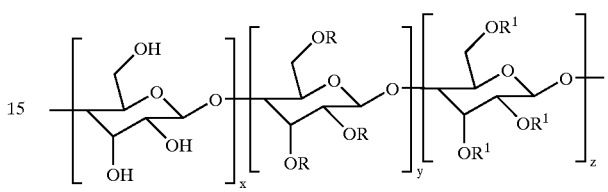

wherein the molecular weight of the polysaccharide prior to modification is defined by the value of the index n which is the sum of the individual units x+y+z. The polysaccharides of the present invention may comprise any linkage; including x to y; x to z; and y to z or mixtures thereof. The above structure also only exemplifies saccharide linkages which are 1,4-linked, however, units having 1,3 links, for example, the formula:

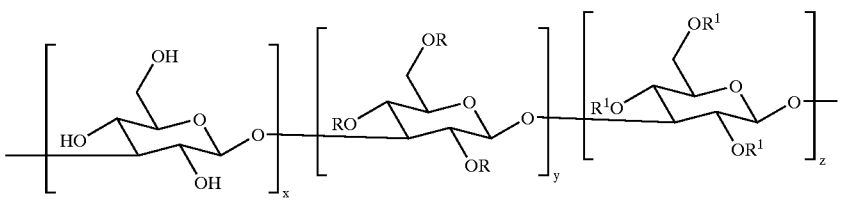

wherein x+y+z=n, are also an aspect of the present invention, as well as 1-6 linkages and mixtures of 1-3, 1-4, and 1-6 linked polysaccharides.

In addition, the residues may comprise acid groups, for example, glucuronic acid units having the formula:

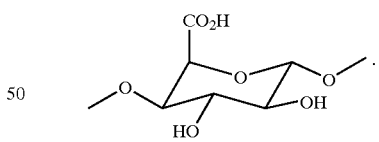

Because any source of polysaccharide will comprise oligomers and/or polymers of mixed length, the index n represents an average value except in the instances wherein the exact number of units can be determined. The index n has an average value of from about 5 to about 6000, however, one aspect of the present invention relates to polysaccharides having an average value of the index n from about 10 to about 3000. Another aspect of the present invention provides embodiments wherein n has an average value of from about 15 to about 1000.

The polysaccharide compounds of the present invention are modified by the substitution of X units that are hydrogen with X units that are either R units or $R^1$ units. R units and $R^1$ units each provide separate fabric benefit enhancing properties. One aspect of the present invention relates to polysaccharide compounds wherein less than 50% of the polysaccharide residues have at least one X unit that is hydrogen replaced by a R or $R^1$ unit. Another aspect of the present invention relates to modified polysaccharide compounds wherein less than 25% of the residues have X units which are R or $R^1$ units, while still another aspect relates to compounds having less than 10% by weight modifications. Other aspects or the present invention, as described herein below, relate to the number of residues which are substituted by R or $R^1$ units, the ratio of R to $R^1$ units present, and the carbon position onto which the substitution takes place (for example, C(2), C(3), or C(6) position).

R units are siloxane comprising units and serve to provide the final compound with a unit which modifies the surface of fabric thereby providing anti-wrinkling benefits. Each R unit independently has the formula:

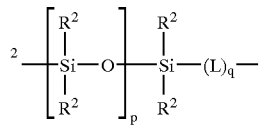

wherein each $R^2$ is independently a $C_1$–$C_{22}$ linear or branched, substituted or unsubstituted hydrocarbyl moiety; an alkyleneamino unit having the formula —$(CH_2)_mN(R^7)_2$ wherein $R^7$ is hydrogen, $C_1$–$C_{12}$ linear or branched, substituted or unsubstituted hydrocarbyl moiety. The length of the silicone containing unit is defined by the index y which itself is also an average value. For example, a discrete mixture of R units having a 50:50 mixture of chains having respectively 7 silicone containing units and 8 silicone containing units will have an average p value of about 6.5. The index p can have an average value of from 0, wherein only an $(R^2)_3Si$— unit is present, to about 50. One aspect of the present invention relates to R units wherein the index p is from 0 to about 20, however, another embodiment comprises R units wherein the index p is from 0 to about 10.

One embodiment of the present invention comprises R units that are a mixture of siloxane units comprising phenyl, $C_1$–$C_{18}$ alkyl, or mixtures thereof. Another aspect of the present invention relates to R units wherein each $R^2$ is independently $C_1$–$C_{12}$ alkyl, and mixtures thereof. In one embodiment of this each aspect $R^2$ is independently $C_1$–$C_6$ alkyl. One embodiment of the present invention comprises R units that entirely comprise $R^2$ units which are methyl.

R units can be directly attached to the polysaccharide backbone, however many aspects of the present invention require the use of a linking unit, L, to facilitate attachment of the siloxane unit to the oligomer or polymer backbone. When a linking unit is present the index q is equal to 1 whereas, when L is absent, q is equal to 0. Any unit that allows attachment of an R unit to the backbone is suitable for use in the present invention, however, one aspect of the present invention utilizes L units independently selected from the group consisting of:

i) —$[C(R^5)_2]_d$—; wherein d is from 1 to 30;
ii) —$[C(R^5)_2]_d(CH=CH)_{d'}$—; wherein d is from 0 to 30; d' is from 1 to 30;
iii) —C(X)—;
iv) —OC(X)—;
v) —C(X)O—;
vi) —$[C(R^5)_2]_eC(X)X(R^6O)_d$—; wherein d is from 0 to 30; e is from 1 to 30;
vii) —$(OR^6)_jXC(X)[C(R^5)_2]_e$—; wherein d is from 0 to 30; e is from 1 to 30;
viii) —$[C(R^5)_2]_eC(X)(R^6O)_j$—; wherein d is from 0 to 30; e is from 1 to 30;
ix) —$(OR^6)_dC(X)[C(R^5)_2]_e$—; wherein d is from 0 to 30; e is from 1 to 30;

x) —$C(X)NR^5$—;
xi) —$C(X)R^6C(X)$—;
xii) —$C(X)NR^5C(X)$—;
xiii) —$C(X)NR^5R^6NR^5C(X)$—;
xiv) —$NR^5C(X)$—;
xv) —$NR^5C(X)NR^5$—;
xvi) —$NR^5C(X)R^6NR^5$—;
xvii) —$NR^5R^6C(X)NR^5$—;
xviii) —$NR^5C(X)R^6C(X)O$—;
xix) —$OC(X)R^6C(X)NR^5$—;
xx) —$NR^5C(X)R^6C(X)O$—;
xxi) —$NR^5C(X)NR^5R^6$—;
xxii) —$R^6NR^5C(X)NR^5$—;
xxiii) —$NR^5C(X)NR^5R^6$—;
xxiv) —$R^6NR^5C(X)NR^5R^6$—;
xxv) —$NR^5$—;
xxvi) —$R^6NR^5$—;
xxvii) —$NR^5R^6$—;
xxviii) —$NR^5N=N$—;
xxix) —$NR^5NR^5$—
xxx) —$OR^6$—;
xxxi) —$R^6O$—;
xxxii) —$R^6OR^6$—;
xxxiii) —$(R^6)_uC(X)(R^6)_u$—;
xxxiv) —$(R^6)_uOC(O)(R^6)_u$—;
xxxv) —$(R^6)_uC(O)O(R^6)_u$—;
xxxvi) —$(R^6)_uOC(O)O(R^6)_u$—;

wherein $R^5$ is hydrogen, $C_1$–$C_{22}$ linear or branched alkyl, $C_1$–$C_{22}$ cycloalkyl, $C_1$–$C_{22}$ linear or branched fluoroalkyl, $C_2$–$C_{22}$ linear or branched alkenyl, $C_6$–$C_{22}$ aryl, $C_7$–$C_{22}$ alkylenearyl, or mixtures thereof, $R^6$ is $C_1$–$C_{30}$ linear or branched, substituted or unsubstituted alkylene; X is oxygen, sulfur, =$NR^5$, or mixtures thereof, u is 0 or 1.

When using one of the above L units, several embodiments of the present invention are especially useful to the formulator. For example, one embodiment of the above linking units relates to the use of glycidyl ether linking units having a moiety of the general formula:

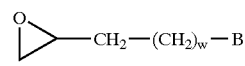

wherein B is a leaving group and the index w has a value such that the total number of continuous carbon atoms in the linking group is from 1 to 30. Non-limiting examples of suitable leaving groups include halogen, tosyl, and the like. When the above glycidyl units are used to attach R units, one embodiment of the present invention can have the formula:

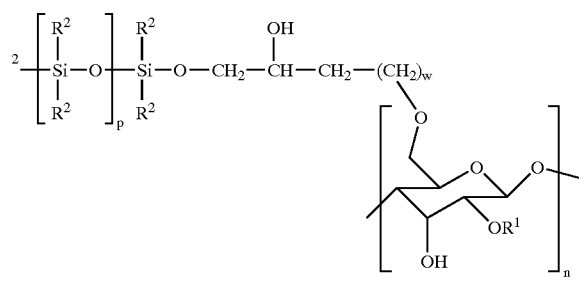

Other ether linking groups include L units having the formula:

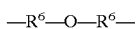

wherein one $R^6$ unit is $C_8$–$C_{30}$ hydroxy substituted linear alkylene unit and one $R^6$ unit is $C_1$–$C_{12}$ alkylene. A non-limiting example of this embodiment includes an L unit having the formula:

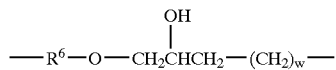

wherein w is from 1 to 27 and $R^6$ can comprise up to 30 continuous carbon atoms.

Another embodiment of the present invention relates to L units having the formula:

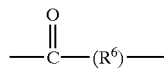

wherein $R^6$ is substituted with one or more —$COOR^{30}$ units; a non-limiting example of which has the formula:

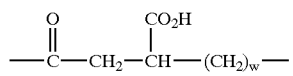

wherein w is from 1 to 27.

$R^1$ units are units which provide the final anti-wrinkle compound with enhanced water dispesibility or enhanced water solubility. There are two types of $R^1$ units according to the present invention: nonionic and anionic units. The $R^1$ units have the formula:

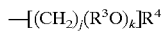

and can be divided into the following groups nonionic, anionic, zwitterionic, and cationic.

Nonionic Groups $R^1$ units are nonionic units when $R^4$ is hydrogen. For the nonionic aspect of the present invention each $R^1$ independently has the formula:

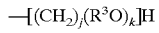

wherein $R^3$ is $C_2$–$C_{12}$ linear or branched alkylene, and mixtures thereof; the index j is from 0 to about 25; and the index k has an average value of from 0 to about 50. One aspect of the present invention derives $R^1$ units from polyalkylene glycols wherein the index j is 0 and in one embodiment k has the average value of from about 3 to about 40.

In one embodiment $R^3$ is $C_2$–$C_6$ linear or branched alkylene, while in another embodiment each $R^3$ unit is ethylene. In this latter case, the formulator may use or modify for use any number of existing polyethyleneoxy oligomers or polymers, for example, polyethyleneglycol having an average molecular weight of 200 daltons (PEG200) k=5; polyethyleneglycol having an average molecular weight 400 daltons (PEG 400) k=9, polyethyleneglycol having an average molecular weight of 1000 daltons (PEG 1000) k=23.

The aspects of the present invention which comprise ethyleneoxy units have an index k with a value of from about 5 to about 30 or from about 5 to about 20 depending upon the exact embodiment.

Another embodiment of the nonionic $R^1$ unit relates to the use of polyalkyleneoxy units wherein $R^3$ is a mixture of alkylene units, for example, block co-polymers of polyethylene glycol and polypropylene glycol (EO/PO co-polymers, wherein said PO unit can be 1,2-propylene, 1,3-propylene, or mixtures thereof), for example Pluronics® available ex BASF. Another embodiment of these mixed block copolymers relates to $R^1$ units which are each independently a mixture of $C_2$–$C_4$ linear or branched alkylene.

However, it is not required for this aspect of the present invention that the index j is equal to 0. The formulator may attach an alkylene unit to the backbone prior to attachment of the alkyleneoxy unit or the alkylene unit may be a part of the nonionic $R^1$ unit.

One aspect of the nonionic $R^1$ unit includes the formation of alkyl ethers, for example, units wherein the index k is equal to 0 and the index j has a value of from 1 to about 12. Another embodiment of this alkyl ether aspect includes methyl and ethyl ethers wherein j has the value 1 and 2 respectively.

The formulator may, for the purposes of adjusting the swelling properties of the bulk material, admix differently modified polysaccharides. For example, a portion of the material may be alkyl ether modified while another portion may be polyalkyleneoxy modified. This aspect of the present invention is described further herein below.

Anionic Groups $R^1$ units are anionic units when $R^4$ comprises a unit capable of having an anionic charge. For the purposes of the present invention any anionic unit is suitable for use as an $R^4$ unit moiety if it provides the required degree of dispersibility or water solubility necessary to achieve the anti-wrinkling benefits of the present invention.

One aspect of the present invention relates to $R^4$ units selected from the group consisting of:
 i) —$CO_2M$;
 ii) —$SO_2M$;
 iii) —$SO_3M$;
 iv) —$OSO_3M$;
 v) —$PO_2M$;
 vi) —$PO_3M$;
 vii) —$OPO_3M$; and
 viii) mixtures thereof;

wherein M is hydrogen or a water soluble cation in a sufficient amount to provide charge neutrality. Non-limiting examples of M units are sodium, potassium, lithium, calcium, magnesium, ammonium, alkylammonium, and the like.

The formulator may also modify the anionic $R^4$ units described herein. For example, sulfonation of a terminal alkylene can result in an anionic unit having the formula —$CH_2(CHSO_3M)CH_2SO_3M$, —$CH_2(CHSO_2M)CH_2SO_3M$, or mixtures thereof.

One embodiment of this aspect of the present invention relates to $R^1$ units each independently having the formula:

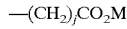

non-limiting examples of which include carboxymethyl, carboxyethyl, and the like.

One aspect of the present invention relates to compounds having less than 50% of said units that are modified. The formula:

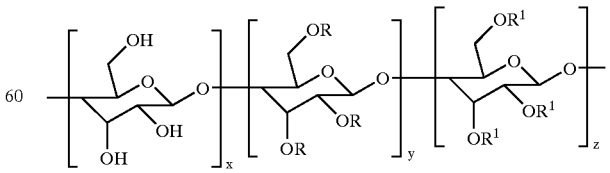

depicts an oligomer or polymer wherein x represents the number of cellulosic units wherein all units are unsubstituted, y represents the number of cellulosic units wherein at least one hydrogen is replaced by an R unit, and z represents the number of cellulosic units wherein at least one hydrogen is replaced by an $R^1$ unit. In the above example, x will be about 50% or greater of the residues.

Another aspect of the present invention relates to cellulosic compounds wherein some residues are substituted by both an R and $R^1$ unit, wherein the formulator can use the differential reactivity of the cellulosic units, either because of their position in the chain, or because of their modified reactivity due to the first substitution, to have some residues with two hydrogens replaced by an R or $R^1$ unit, for example, having the formula:

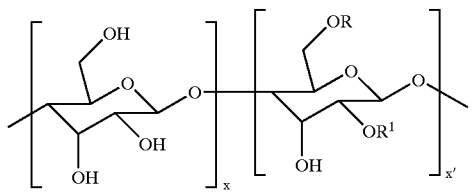

wherein x' represents the number of cellulosic units having two hydrogens replaced by a R or $R^1$ unit, and x+x'=n One aspect of the present invention relates to cellulosic compounds having the following ratios of substitution:

| x  | y  | Z  |
|----|----|----|
| 50 | 25 | 25 |
| 70 | 15 | 15 |
| 80 | 10 | 10 |
| 85 | 10 | 5  |
| 90 | 5  | 5  |
| 95 | 3  | 2  |
| 97 | 1  | 2  | x equals number of residues having all hydroxyl units.
y equals number of residues having one hydrogen replaced by an R unit.
Z equals number of residues having one hydrogen replaced by an $R^1$ unit.

Zwitterionic/Cationic Groups

Alternately, $R^1$ units are zwitterionic or cationic units when the polysaccharide derivative comprises units capable of having cationic charge alone or in conjunction with an anionic charge. For the purposes of the present invention, any cationic unit along with any anionic unit is suitable for use if it provides the required degree of dispersibility or water solubility necessary to achieve the anti-wrinkling benefits of the present invention.

Formulations

One aspect of the present invention relates to compositions which comprise the modified polysaccharide oligomers or polymers. A first embodiment relates to compositions which deliver through the wash anti-wrinkle benefits. Formulations of this aspect can be modified for use at any step in the laundry cycle, for example, as a pre-soak, as an addition to surfactant comprising compositions, as a rinse-added composition. Non-limiting examples of compositions which comprise this aspect comprise:
   a) from about 0.01% to about 99% by weight, of one or more modified polysaccharides according to the present invention. Another embodiment comprises from about 0.1% to about 50% by weight of said modified polysaccharide, while yet another embodiment comprises from about 0.5% to about 5% by weight, of the anti-wrinkle component; and
   b) the balance a suitable carrier.

Another embodiment of this aspect comprises in addition to a suitable carrier other adjunct ingredients which can enhance the anti-wrinkle effectiveness of the modified polysaccharides or which enhance the delivery of said polysaccharides to fabric surface.

The compositions of the present invention further relate to the aspect of detersive surfactant comprising compositions, said compositions comprising:
   a) from about 0.01% to about 30% by weight, of one or more modified polysaccharides according to the present invention. Another embodiment comprises from about 0.1% to about 10% by weight of said modified polysaccharide, while yet another embodiment comprises from about 0.5% to about 5% by weight, of the anti-wrinkle component;
   b) from about 10% by weight, in one embodiment from about 10% to about 80% by weight, in yet another embodiment from about 10% to about 60%, wherein another embodiment comprises from about 15% to about 30% by weight, of a surfactant system, said surfactant system comprising:
      i) from about 0.01%, whereas depending upon which aspect or embodiment of the present invention, the following ranges are suitable: from about 0.1% to about 100%; from about 1% to about 80%; from about 1% to about 60%, from about 1% to about 30% by weight, of one or more anionic surfactants, said anionic surfactants selected form the group consisting of linear alkyl benzene sulphonates, mid-chain branched alkyl benzene sulphonates; linear alkyl sulfates, mid-chain branched sulfates, linear alkyleneoxy sulfates, mid-chain branched alkyleneoxy sulfates; and mixtures thereof;
      ii) optionally, from about 0.01%, whereas depending upon which aspect or embodiment of the present invention, the following ranges are suitable: from about 0.1% to about 100%; from about 1% to about 80%; from about 1% to about 60%, from about 1% to about 30% by weight, of one or more nonionic surfactants selected from the group consisting of alcohols, alcohol ethoxylates, polyoxyalkylene alkylamides, and mixtures thereof; and
   c) the balance carriers and other adjunct ingredients.

One embodiment of this aspect of the present invention relates to surfactant systems comprising:
   i) from about 0.01% by weight, of a surfactant selected from the group consisting of alkyl sulfate surfactants, alkoxy sulfate surfactants, mid-chain branched alkyl sulfate surfactants, mid-chain branched alkoxy sulfate surfactants, mid-chain branched aryl sulfonate surfactants, and mixtures thereof;
   ii) from about 0.01% by weight, of one or more aryl sulphonate anionic surfactants;
   iii) from about 0.01% by weight, of one or more nonionic surfactants.

A further embodiment relates to compositions comprising:
   i) from about 0.01% by weight, of a surfactant selected from the group consisting of alkyl sulfate surfactants, alkoxy sulfate surfactants, and mixtures thereof;
   ii) from about 0.01% by weight, of one or more nonionic surfactants which are alkylethoxylates, alkyl alcohols, and mixtures thereof.

Surfactants

As described hereinabove, one aspect of the present invention relates to compositions comprising a surfactant system. The surfactant systems of the present invention may comprise any type of detersive surfactant, non-limiting examples of which include one or more mid-chain branched alkyl sulfate surfactants, one or more mid-chain branched alkyl alkoxy sulfate surfactants, one or more mid-chain branched aryl sulfonate surfactants, one or more non mid-chain branched sulphonates, sulphates, cationic surfactants, zwitterionic surfactants, ampholytic surfactants, and mixtures thereof.

The total amount of surfactant present in the compositions of the present invention is from about 10% by weight, in one embodiment of the present invention the range of surfactant is from about 10% to about 80% by weight, of said composition. Another embodiment the amount of surfactant is from about 10% to about 60%, wherein another embodiment comprises from about 15% to about 30% by weight, of said composition.

Nonlimiting examples of surfactants useful herein include:
a) $C_{11}$–$C_{18}$ alkyl benzene sulfonates (LAS);
b) $C_6$–$C_{18}$ mid-chain branched aryl sulfonates (BLAS);
c) $C_{10}$–$C_{20}$ primary, $C_{10}$–$C_{20}$-branched, and random alkyl sulfates (AS);
d) $C_{14}$–$C_{20}$ mid-chain branched alkyl sulfates (BAS);
e) $C_{10}$–$C_{18}$ secondary (2,3) alkyl sulfates as described in U.S. Pat. No. 3,234,258 Morris, issued Feb. 8, 1966; U.S. Pat. No. 5,075,041 Lutz, issued Dec. 24, 1991; U.S. Pat. No. 5,349,101 Lutz et al., issued Sep. 20, 1994; and U.S. Pat. No. 5,389,277 Prieto, issued Feb. 14, 1995;
f) $C_{10}$–$C_{18}$ alkyl alkoxy sulfates ($AE_xS$) wherein preferably x is from 1–7;
g) $C_{14}$–$C_{20}$ mid-chain branched alkyl alkoxy sulfates ($BAE_xS$);
h) $C_{10}$–$C_{18}$ alkyl alkoxy carboxylates preferably comprising 1–5 ethoxy units;
i) $C_{12}$–$C_{18}$ alkyl ethoxylates, $C_6$–$C_{12}$ alkyl phenol alkoxylates wherein the alkoxylate units are a mixture of ethyleneoxy and propyleneoxy units, $C_{12}$–$C_{18}$ alcohol and $C_6$–$C_{12}$ alkyl phenol condensates with ethylene oxide/propylene oxide block polymers inter alia Pluronic® ex BASF which are disclosed in U.S. Pat. No. 3,929,678 Laughlin et al., issued Dec. 30, 1975;
j) $C_{14}$–$C_{22}$ mid-chain branched alkyl alkoxylates, $BAE_x$;
k) Alkylpolysaccharides as disclosed in U.S. Pat. No. 4,565,647 Llenado, issued Jan. 26, 1986;
l) Pseudoquat surfactants having the formula:

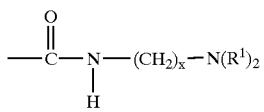

wherein R is $C_4$–$C_{10}$ alkyl, $R^1$ is selected from the group consisting of $C_1$–$C_4$ alkyl, —$(CH_2CHR^2O)_yH$, and mixtures thereof; $R^2$ is hydrogen, ethyl, methyl, and mixtures thereof; y is from 1 to 5; x is from 2 to 4; for the purposes of the present invention, a particularly useful pseudoquat surfactant comprises R equal to an admixture of $C_8$–$C_{10}$ alkyl, $R^1$ is equal to methyl; and x equal to 3; these surfactants are described in U.S. Pat. No. 5,916,862 Morelli et al., issued Jun. 29, 1999;
m) Polyhydroxy fatty acid amides having the formula:

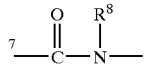

wherein $R^7$ is $C_5$–$C_{31}$ alkyl; $R^8$ is selected from the group consisting of hydrogen, $C_1$–$C_4$ alkyl, $C_1$–$C_4$ hydroxyalkyl, Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. These surfactants are described in U.S. Pat. No. 5,489,393 Connor et al., issued Feb. 6, 1996; and U.S. Pat. No. 5,45,982 Murch et al., issued Oct. 3, 1995.

The mid-chain branched alkyl sulfate surfactants of the present invention have the formula:

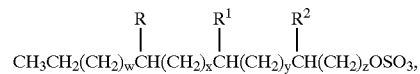

the alkyl alkoxy sulfates have the formula:

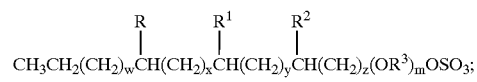

the alkyl alkoxylates have the formula:

wherein R, $R^1$, and $R^2$ are each independently hydrogen, $C_1$–$C_3$ alkyl, and mixtures thereof; provided at least one of R, $R^1$, and $R^2$ is not hydrogen; preferably R, $R^1$, and $R^2$ are methyl; preferably one of R, $R^1$, and $R^2$ is methyl and the other units are hydrogen. The total number of carbon atoms in the mid-chain branched alkyl sulfate and alkyl alkoxy sulfate surfactants is from 14 to 20; the index w is an integer from 0 to 13; x is an integer from 0 to 13; y is an integer from 0 to 13; z is an integer of at least 1; provided w+x+y+z is from 8 to 14 and the total number of carbon atoms in a surfactant is from 14 to 20; $R^3$ is $C_1$–$C_4$ linear or branched alkylene, preferably ethylene, 1,2-propylene, 1,3-propylene, 1,2-butylene, 1,4-butylene, and mixtures thereof.

M denotes a cation, preferably hydrogen, a water soluble cation, and mixtures thereof. Non-limiting examples of water soluble cations include sodium, potassium, lithium, ammonium, alkyl ammonium, and mixtures thereof.

Adjunct Ingredients

The following are non-limiting examples of adjunct ingredients useful in the laundry compositions of the present invention, said adjunct ingredients include builders, optical brighteners, soil release polymers, dye transfer agents, dispersants, enzymes, suds suppressers, dyes, perfumes, colorants, filler salts, hydrotropes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

Builders

The laundry detergent compositions of the present invention preferably comprise one or more detergent builders or builder systems. When present, the compositions will typically comprise at least about 1% builder, another embodiment comprises from 5% to about 80% by weight of a builder. Other embodiments comprise from about 10% to about 30% by weight, of detergent builder preferably to about 50%, more preferably.

Inorganic or P-containing detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Examples of silicate-builders are the alkali metal silicates, examples of which include those having a $SiO_2:Na_2O$ ratio in the range 1.6:1 to 3.2:1 and layered silicates as described in U.S. Pat. No. 4,664,839 Rieck, issued May 12, 1987 which include NaSKS-6® ex Hoechst. Others include NaSKS-5®, NaSKS-7®, and NaSKS-11® also ex Hoechst.

Examples of carbonate builders are the alkaline earth and alkali metal carbonates as disclosed in German Patent Application No. 2,321,001 published on Nov. 15, 1973.

Aluminosilicate builders include those having the empirical formula:

$$[M_z(zAlO_2)_y]xH_2O$$

wherein z and y are integers of at least 6, the molar ratio of z to y is in the range from 1.0 to about 0.5, and x is an integer from about 15 to about 264, known as Zeolite A, Zeolite P (B), Zeolite MAP and Zeolite X. In one embodiment, the crystalline aluminosilicate ion exchange material has the formula:

$$Na_{12}[(AlO_2)_{12}(SiO_2)_{12}]xH_2O$$

wherein x is from about 20 to about 30, especially about 27. This material is known as Zeolite A. Preferably, the aluminosilicate has a particle size of about 0.1–10 microns in diameter.

Included among the polycarboxylate builders are those disclosed in U.S. Pat. No. 3,128,287 Berg, issued Apr. 7, 1964, and U.S. Pat. No. 3,635,830 Lamberti et al., issued Jan. 18, 1972; U.S. Pat. No. 4,663,071 Bush et al., issued May 5, 1987; U.S. Pat. No. 3,923,679 Rapko, issued Dec. 2, 1975; U.S. Pat. No. 4,158,635 Crutchfield et al., issued Jun. 19, 1979; U.S. Pat. No. 4,120,874 Crutchfield et al., issued Oct. 17, 1978; and U.S. Pat. No. 4,102,903 Crutchfield et al., issued Jul. 25, 1978.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations due to their availability from renewable resources and their biodegradability. Citrates can also be used in granular compositions, especially in combination with zeolite and/or layered silicate builders. Oxydisuccinates are also especially useful in such compositions and combinations.

Other suitable builders are disclosed in U.S. Pat. No. 4,566,984, Bush, issued Jan. 28, 1986; U.S. Pat. No. 4,144,226, Crutchfield et al., issued Mar. 13, 1979 and in U.S. Pat. No. 3,308,067, Diehl, issued Mar. 7, 1967 and U.S. Pat. No. 3,723,322.

Fatty acids, e.g., $C_{12}$–$C_{18}$ monocarboxylic acids, can also be incorporated into the compositions alone, or in combination with the aforesaid builders. In embodiments wherein phosphorus-based builders are used the various alkali metal phosphates, inter alia, sodium tripolyphosphates, sodium pyrophosphate and sodium orthophosphate can be used. Phosphonate builders such as ethane-1-hydroxy-1,1-diphosphonate and other known phosphonates as described in U.S. Pat. Nos. 3,159,581; 3,213,030; 3,422,021; 3,400,148 and 3,422,137.

Dispersants

The compositions of the present invention may comprise from about 0.01% to about 10% by weight of one or more polyalkyleneimine dispersants as described in U.S. Pat. No. 4,597,898 Vander Meer, issued Jul. 1, 1986; European Patent Application 111,965 Oh and Gosselink, published Jun. 27, 1984; European Patent Application 111,984 Gosselink, published Jun. 27, 1984; European Patent Application 112,592 Gosselink, published Jul. 4, 1984; U.S. Pat. No. 4,548,744 Connor, issued Oct. 22, 1985; and U.S. Pat. No. 5,565,145 Watson et al., issued Oct. 15, 1996. However, any suitable clay/soil dispersant or anti-redepostion agent can be used in the laundry compositions of the present invention.

The compositions of the present invention may comprise from about 0.01% to about 10% by weight, of one or more polymeric polycarboxylates and polyethylene glycols, for example, those derived from acrylic acid, maleic acid (or maleic anhydride), fumaric acid, itaconic acid, aconitic acid, mesaconic acid, citraconic acid and methylenemalonic acid. These monomers can be used alone, in combination with each other monomers or in combination of units such as vinylmethyl ether, styrene, ethylene, etc. provided that such segments do not constitute more than about 40% by weight, of said polymer.

One embodiment comprises from about 0.01% to about 10% by weight, polymeric polycarboxylates derived from acrylic acid having an average molecular weight of from about 2,000 to 10,000, or in another embodiment from about 4,000 to 7,000 or from about 4,000 to 5,000. Polyacrylates of this type are disclosed in U.S. Pat. No. 3,308,067 Diehl, issued Mar. 7, 1967. In addition, acrylic/maleic-based copolymers having average molecular weights ranging from about 2,000 to 100,000 are useful. However, depending upon the embodiment, molecular weight ranges may include from about 5,000 to 75,000, and from about 7,000, to 65,000. The ratio of acrylate to maleate segments in such copolymers will generally range from about 30:1 to about 1:1, however, about 10:1 to 2:1 is also useful as a further embodiment. Acrylate/maleate copolymers described in European Patent Application No. 66915, published Dec. 15, 1982, and EP 193,360, published Sep. 3, 1986.

A further embodiment comprises from about 0.01% to about 10% by weight, of polyethylene glycol (PEG) having molecular weight ranges of from about 500 to about 100,000; from about 1,000 to about 50,000; and from about 1,500 to about 10,000.

Soil Release Agents

The compositions according to the present invention may optionally comprise one or more soil release agents. If utilized, soil release agents will generally comprise from about 0.01% to about 10% by weight of the composition, however, one embodiment comprises from about 0.1% to about 5% by weight of said composition, whereas other embodiments comprise from about 0.2% to about 3% by weight, of the composition.

Polymers suitable for use in the present invention are described in U.S. Pat. No. 5,843,878 Gosselink et al., issued Dec. 1, 199; U.S. Pat. No. 5,834,412 Rohrbaugh et al., issued Nov. 10, 1998; U.S. Pat. No. 5,728,671 Rohrbaugh et al., issued Mar. 17, 1998; U.S. Pat. No. 5,691,298 Gosselink et al., issued Nov. 25, 1997; U.S. Pat. No. 5,599,782 Pan et al., issued Feb. 4, 1997; U.S. Pat. No. 5,415,807 Gosselink et al., issued May 16, 1995; U.S. Pat. No. 5,182,043 Morrall et al., issued Jan. 26, 1993; U.S. Pat. No. 4,956,447 Gosselink et al., issued Sep. 11, 1990; U.S. Pat. No. 4,976,879 Maldonado et al., issued Dec. 11, 1990; U.S. Pat. No. 4,968,451 Scheibel et al., issued Nov. 6, 1990; U.S. Pat. No. 4,925,577 Borcher, Sr. et al., issued May 15, 1990; U.S. Pat. No. 4,861,512 Gosselink, issued Aug. 29, 1989; U.S. Pat. No. 4,877,896 Maldonado et al., issued Oct. 31, 1989; U.S.

Pat. No. 4,771,730 Gosselink et al., issued Oct. 27, 1987; U.S. Pat. No. 711,730 Gosselink et al., issued Dec. 8, 1987; U.S. Pat. No. 4,721,580 Gosselink issued Jan. 26, 1988; U.S. Pat. No. 4,000,093 Nicol et al., issued Dec. 28, 1976; U.S. Pat. No. 3,959,230 Hayes, issued May 25, 1976; U.S. Pat. No. 3,893,929 Basadur, issued Jul. 8, 1975; and European Patent Application 0 219 048, published Apr. 22, 1987 by Kud et al.

Further suitable soil release agents are described in U.S. Pat. No. 4,201,824 Voilland et al.; U.S. Pat. No. 4,240,918 Lagasse et al.; U.S. Pat. No. 4,525,524 Tung et al; U.S. Pat. No. 4,579,681 Ruppert et al.; U.S. Pat. No. 4,220,918; U.S. Pat. No. 4,787,989; EP 279,134 A, 1988 to Rhone-Poulenc Chemie; EP 457,205 A to BASF (1991); and DE 2,335,044 to Unilever N.V., 1974.

Method of Use

The present invention further relates to a method for providing anti-wrinkle benefits to fabric, preferably clothing, said method comprising the step of contacting fabric in need of cleaning with an aqueous solution of a laundry detergent composition comprising:

a) from about 0.01% to about 30% by weight, of the anti-wrinkle component.

b) from about 10% by weight, of a surfactant system, said surfactant system comprising:

i) from about 0.01% by weight, of one or more anionic surfactants, said anionic surfactants selected form the group consisting of linear alkyl benzene sulphonates, mid-chain branched alkyl benzene sulphonates; linear alkyl sulfates, mid-chain branched sulfates, linear alkyleneoxy sulfates, mid-chain branched alkyleneoxy sulfates; and mixtures thereof; and ii) optionally, from about 0.01% by weight, of one or more nonionic surfactants selected from the group consisting of alcohols, alcohol ethoxylates, polyoxyalkylene alkylamides, and mixtures thereof; and c) the balance carriers and other adjunct ingredients.

The compositions of the present invention can be suitably prepared by any process chosen by the formulator, non-limiting examples of which are described in U.S. Pat. No. 5,691,297 Nassano et al., issued Nov. 11, 1997; U.S. Pat. No. 5,574,005 Welch et al., issued Nov. 12, 1996; U.S. Pat. No. 5,569,645 Dinniwell et al., issued Oct. 29, 1996; U.S. Pat. No. 5,565,422 Del Greco et al., issued Oct. 15, 1996; U.S. Pat. No. 5,516,448 Capeci et al., issued May 14, 1996; U.S. Pat. No. 5,489,392 Capeci et al., issued Feb. 6, 1996; U.S. Pat. No. 5,486,303 Capeci et al., issued Jan. 23, 1996 all of which are incorporated herein by reference.

EXAMPLES

The following are non-limiting examples of procedures for preparing the silicon comprising modified polysaccharides of the present invention.

Example 1

To a 3 L flask is charged finely ground birch cellulose (60 g), ethanol (420 mL), isopropanol (420 mL) and water (42 mL). The solution is stirred for 30 minutes after which time NaOH (12 g of a 50% w/w solution) is added over 5 minutes. After stirring an additional 30 minutes, (3-glycidoxypropyl) pentamethylsiloxane (2.4 g) is added over 5 minutes after which the reaction is heated to 70° C. for two hours. The flask is cooled to room temperature and NaOH (31 g of a 50% w/w solution) is added over 5 minutes. Once the reaction has stirred an additional 30 minutes monochloroacetic acid (30 g of an 80% aqueous solution) is added slowly and the resulting solution heated to 70° C. for 1 hour. After cooling, the solids are removed by filtration, washed with ethanol (500 mL) and dried under vacuum to yield the desired modified cellulose.

Example 2

To a 3 L flask is charged finely ground birch cellulose (50 g), ethanol (350 mL), isopropanol (350 mL) and water (35 mL). The solution is stirred for 30 minutes after which time NaOH (48.5 g of a 50% w/w solution) is added over 5 minutes. After stirring an additional 30 minutes, monochloro acetic acid (25 g of an 80% aqueous solution) and 3-chloropropyltrimethylsilane (5 g) is added over 5 minutes after which the reaction is heated to 70° C. for two hours. After cooling, the solids are removed by filtration, washed with ethanol (500 mL) and dried under vacuum to yield the desired modified cellulose.

Example 3

To a 2 L flask is charged potato starch (45 g) and methanol (75 mL). The solution is stirred for 10 minutes after which time NaOH (26.5 g of a 50% w/w solution) is added over 5 minutes. After stirring an additional 2 hrs, (3-glycidoxypropyl) pentamethylsiloxane (2.4 g) is added over 5 minutes after which the reaction is heated to 60° C. for three hours. Next, monochloroacetic acid (19 g of an 80% aqueous solution) is added slowly and the resulting solution heated at 60° C. for 3 hours. After cooling, the reaction was slurried in 200 ml isopropanol and the solids are removed by filtration, washed with methanol (200 mL) and dried under vacuum to yield the desired modified starch.

Example 4

To a 3 L flask is charged guar flour (45 g), isopropanol (100 mL) and water (30 mL). The solution is stirred for 30 minutes after which time NaOH (30 g of a 50% w/w solution) is added over 5 minutes. After stirring an additional 30 minutes, monochloro acetic acid (19 g of an 80% aqueous solution) and 3-chloropropyltrimethylsilane (5 g) is added over 5 minutes after which the reaction is heated to 70° C. for two hours. After cooling, the solids are removed by filtration, washed with ethanol (500 mL) and dried under vacuum to yield the desired modified guar.

The following are non-limiting examples of compositions according to the present invention.

TABLE I

| | weight % | | | |
|---|---|---|---|---|
| Ingredients | 5 | 6 | 7 | 8 |
| Polyhydroxy coco-fatty acid amide | 2.50 | 4.00 | 4.50 | — |
| NEODOL 24-7[1] | — | 4.50 | — | — |
| NEODOL 23-9[2] | 0.63 | — | 4.50 | 2.00 |
| $C_{12}$–$C_{15}$ Alkyl ethoxylate sulphate | 20.15 | 4.00 | 5.50 | 20.50 |
| $C_{12}$–$C_{15}$ Alkyl sulfate | — | 14.00 | 15.00 | — |
| C11.8 linear alkylbenzene sulfonate | — | — | — | 6.00 |
| $C_8$–$C_{10}$-Amidopropyl Amine | — | 1.30 | — | — |
| $C_{10}$-Amidopropyl Amine | 0.50 | — | — | 1.50 |
| Citric acid | 3.00 | 2.00 | 3.00 | 2.50 |
| $C_{12}$–$C_{18}$ fatty acid | 2.00 | 6.50 | 5.00 | 5.00 |
| Rapeseed fatty acid | — | 4.10 | — | 6.50 |
| Ethanol | 3.36 | 1.53 | 5.60 | 0.50 |
| Propanediol | 7.40 | 9.20 | 6.22 | 4.00 |
| Monoethanolamine | 1.00 | 7.90 | 8.68 | 0.50 |
| Sodium hydroxide | 2.75 | 1.30 | 0.75 | 4.40 |
| Sodium p-toluene sulfonate | 2.25 | — | 1.90 | — |
| Borax/Boric acid | 2.50 | 2.00 | 3.50 | 2.50 |
| Protease[3] | 0.88 | 0.74 | 1.50 | 0.88 |
| Lipolase[4] | — | 0.12 | 0.18 | — |

TABLE I-continued

| Ingredients | weight % | | | |
|---|---|---|---|---|
| | 5 | 6 | 7 | 8 |
| Duramyl[5] | 0.15 | 0.11 | — | 0.15 |
| CAREZYME | 0.053 | 0.028 | 0.080 | 0.053 |
| Dispersant[6] | 0.60 | 0.70 | 1.50 | 0.60 |
| Ethoxylated polyalkyleneimine[7] | 1.20 | 0.70 | 1.50 | 1.20 |
| Optical Brightener | 0.13 | 0.15 | 0.30 | 0.15 |
| Polyamine[8] | 5.00 | 1.00 | — | — |
| Polyamine[9] | — | — | 0.25 | 0.50 |
| Anti-wrinkle agent[10] | | | | |
| Suds suppresser | 0.12 | 0.28 | 0.12 | 0.12 |
| Minors, aesthetics, stabilizers, water | balance | balance | balance | balance |

[1]$C_{12}$–$C_{14}$ alkyl ethoxylate as sold by Shell Oil Co.
[2]$C_{12}$–$C_{13}$ alkyl ethoxylate as sold by Shell Oil Co.
[3]Protease B variant of BPN' wherein Tyr 17 is replaced with Leu.
[4]Derived from *Humicola lanuginosa* and commercially available from Novo.
[5]Disclosed in WO 9510603 A and available from Novo.
[6]Hydrophilic dispersant PEI 189 $E_{15}$–$E_{18}$ according to U.S. Pat. No. 4,597,898, Vander Meer, issued Jul. 1, 1986.
[7]Polyalkyleneimine dispersant PEI 600 $E_{20}$.
[8]Lupasol ® SK ex BASF.
[9]Lupasol ® SKA ex BASF.
[10]According to Example 1.

TABLE II

| Ingredients | weight % | | |
|---|---|---|---|
| | 9 | 10 | 11 |
| Anionic surfactant[1] | 28.69 | 28.99 | 34.80 |
| Nonionic surfactant[2] | 5.93 | 5.93 | — |
| Cationic surfactant[3] | — | — | 5.51 |
| Bleach activator system[4] | 6.10 | 6.10 | 4.53 |
| Photobleach[5] | 0.03 | 0.03 | 0.03 |
| Suds supressor[6] | 3.46 | 3.46 | 1.89 |
| Builder[7] | 6.75 | 6.75 | — |
| Builder[8] | 14.67 | 14.67 | 10.68 |
| Dye transfer inhibitor[9] | 0.14 | 0.14 | — |
| Perfume[10] | 0.25 | 0.25 | — |
| $C_{12}$–$C_{15}$ alkyl ethoxy (7.0) alcohol[11] spray on | 5.82 | 5.82 | — |
| PEG 200[12] | — | 1.2 | — |
| Zwitterionic hexamethylene diamine[13] | 1.50 | 1.25 | 1.08 |
| Optical brightener | 0.28 | 0.28 | 0.183 |
| Sodium carbonate | 5.02 | 5.02 | 13.96 |
| Sodium perborate | 17.80 | 17.80 | — |
| Sodium percarbonate | — | — | 14.33 |
| Sodium HEDP | 0.85 | 0.85 | — |
| Anti-wrinkle agent | | | |
| Perfume | 0.35 | 0.35 | 0.46 |
| Protease enzyme | 0.92 | 0.92 | 0.89 |
| Cellulase enzyme | 0.27 | 0.27 | 0.21 |
| Lipase enzyme | 0.23 | 0.23 | 0.275 |
| Amylase enzyme | 0.75 | 0.75 | 1.04 |
| Citric acid | — | — | 7.16 |
| Soil release polymer[14] | 0.50 | 0.50 | 0.50 |
| Minors[15] | balance | balance | balance |

[1]Anionic surfactant agglomeration comprising 38% surfactant, 22% zeolite, 40% sodium carbonate.
[2]Nonionic surfactant agglomeration comprising 26% surfactant, 48% zeolite, 26% sodium carbonate.
[3]Cationic surfactant agglomeration comprising 24% surfactant, 64% zeolite, 12% sodium sulphate.
[4]Bleach activator system comprising 81% TAED, 17% acrylic/maleic copolymer (acid form), 2% moisture.
[5]Encapsulated zinc phthalocyanine (10%) according to U.S. Pat. No. 4,033,718, Holcombe et al., issued Jul. 5, 1977.
[6]Zeolite.
[7]Admixture comprising 11.5% silicone oil ex Dow Corning and 88.5% starch.
[8]Layered silicate comprising 78% SKS-6 ex Hoechst and 22% citric acid.
[9]Dye transfer inhibitor agglomerate comprises 21% PVNO/PVPVI, 61% zeolite and 18% sodium carbonate.
[10]Perfume encapsulate comprises 50% perfume and 50% starch.
[11]$C_{12}$–$C_{15}$ alkyl ethoxy (7.0) alcohol and 17% by weight, of polyethylene glycol having an average molecular weight of about 4000.
[12]Polyethylene glycol having an average molecular weight of 200.
[13]According to Example 1.
[14]Soil release polymer according to U.S. Pat. No. 5,415,807 Gosselink et al., issued May 16, 1995.
[15]Balance to 100% can, for example, include minors like, processing aids, additional water, and fillers, including $CaCO_3$, talc, silicates, etc.

What is claimed is:

1. A compound having the formula:

$$\left[\begin{array}{c} OH \\ \diagup\!\!\!\diagdown\!\!\!-O- \\ OH \quad OH \end{array}\right]_x \left[\begin{array}{c} OR \\ \diagup\!\!\!\diagdown\!\!\!-O- \\ OR \quad OR \end{array}\right]_y \left[\begin{array}{c} OR^1 \\ \diagup\!\!\!\diagdown\!\!\!-O- \\ OR^1 \quad OR^1 \end{array}\right]_z$$

wherein each R unit is independently a siloxane unit having the formula:

$$-\left[\begin{array}{c} R^2 \\ | \\ Si-O \\ | \\ R^2 \end{array}\right]_p \begin{array}{c} R^2 \\ | \\ Si-(L)_q- \\ | \\ R^2 \end{array}$$

wherein each $R^2$ is independently a $C_1$–$C_{22}$ linear or branched, substituted or unsubstituted hydrocarbyl moiety; the index p is from 0 to about 50; L is a linking group; the index q is 0 or 1; each $R^1$ unit is independently a fabric substantive unit having the formula:

$$-[(CH_2)_j(R^3O)_k]R^4$$

wherein $R^3$ is $C_2$–$C_{12}$ linear or branched alkylene; $R^4$ is hydrogen, an anionic unit, and mixtures thereof; the index j is from 0 to about 25; the index k is from 0 to about 50; the sum of the indices x+y+z=n wherein n has an average value of from 5 to about 6000.

2. The compound of claim 1 wherein each $R^2$ is independently phenyl, $C_1$–$C_{18}$ alkyl, or mixtures thereof.

3. The compound of claim 2 wherein each $R^2$ is independently $C_1$–$C_{12}$ alkyl, or mixtures thereof.

4. The compound of claim 3 wherein each $R^2$ is independently $C_1$–$C_6$ alkyl, or mixtures thereof.

5. The compound of claim 1 wherein the index p is from 0 to about 20.

6. The compound of claim 5 wherein the index p is from 0 to about 10.

7. The compound of claim 1 wherein L is a linking group selected from the group consisting of:

i) $-[C(R^5)_2]_d-$; wherein d is from 1 to 30;
  ii) $-[C(R^5)_2]_d(CH=CH)_{d'}-$; wherein d is from 0 to 30; d' is from 1 to 30;
  iii) $-C(X)-$;
  iv) $-OC(X)-$;
  v) $-C(X)O-$;
  vi) $-[C(R^5)_2]_eC(X)X(R^6O)_d-$; wherein d is from 0 to 30; e is from 1 to 30;

vii) $-(OR^6)_j XC(X)[C(R^5)_2]_e-$; wherein d is from 0 to 30; e is from 1 to 30;
viii) $-[C(R^5)_2]_e C(X)(R^6O)_j-$; wherein d is from 0 to 30; e is from 1 to 30;
ix) $-(OR^6)_d C(X)[C(R^5)_2]_e-$; wherein d is from 0 to 30; e is from 1 to 30;
x) $-C(X)NR^5-$;
xi) $-C(X)R^6C(X)-$;
xii) $-C(X)NR^5C(X)-$;
xiii) $-C(X)NR^5R^6NR^5C(X)-$;
xiv) $-NR^5C(X)-$;
xv) $-NR^5C(X)NR^5-$;
xvi) $-NR^5C(X)R^6NR^5-$;
xvii) $-NR^5R^6C(X)NR^5-$;
xviii) $-NR^5C(X)R^6C(X)O-$;
xix) $-OC(X)R^6C(X)NR^5-$;
xx) $-NR^5C(X)R^6C(X)O-$;
xxi) $-NR^5C(X)NR^5R^6-$;
xxii) $-R^6NR^5C(X)NR^5-$;
xxiii) $-NR^5C(X)NR^5R^6-$;
xxiv) $-R^6NR^5C(X)NR^5R^6-$;
xxv) $-NR^5-$;
xxvi) $-R^6NR^5-$;
xxvii) $-NR^5R^6-$;
xxviii) $-NR^5N=N-$;
xxix) $-NR^5NR^5-$
xxx) $-OR^6-$;
xxxi) $-R^6O-$;
xxxii) $-R^6OR^6-$;
xxxiii) $-(R^6)_u C(X)(R^6)_u-$;
xxxiv) $-(R^6)_u OC(O)(R^6)_u-$;
xxxv) $-(R^6)_u C(O)O(R^6)_u-$; and
xxxvi) $-(R^6)_u OC(O)O(R^6)_u-$;
wherein $R^5$ is hydrogen, $C_1$–$C_{22}$ linear or branched alkyl, $C_1$–$C_{22}$ cycloalkyl, $C_1$–$C_{22}$ linear or branched fluoroalkyl, $C_2$–$C_{22}$ linear or branched alkenyl, $C_6$–$C_{22}$ aryl, $C_7$–$C_{22}$ alkylenearyl, or mixtures thereof; $R^6$ is $C_1$–$C_{30}$ linear or branched, substituted or unsubstituted alkylene; X is oxygen, sulfur, $=NR^5$, or mixtures thereof; and u is 0 or 1.

8. The compound of claim 7 wherein the unit which substitutes the alkylene unit is selected from the group consisting of:
i) $-NHCOR^{30}$;
ii) $-COR^{30}$;
iii) $-COOR^{30}$;
iv) $-COCH=CH_2$;
v) $-C(=NH)NH_2$;
vi) $-N(R^{30})_2$;
vii) $-NHC_6H_5$;
viii) $=CHC_6H_5$;
ix) $-CON(R^{30})_2$;
x) $-CONHNH_2$;
xi) $-NHCN$;
xii) $-OCN$;
xiii) $-CN$;
xiv) F, Cl, Br, I, and mixtures thereof;
xv) $=O$;
xvi) $-OR^{30}$;
xvii) $-NHCHO$;
xviii) $-OH$;
xix) $-NHN(R^{30})_2$;
xx) $=NR^{30}$;
xxi) $=NOR^{30}$;
xxii) $-NHOR^{30}$;
xxiii) $-CNO$;
xxiv) $-NCS$;
xxv) $=C(R^{30})_2$;
xxvi) $-SO_3M$;
xxvii) $-OSO_3M$;
xxviii) $-SCN$;
xxix) $-P(O)H_2$;
xxx) $-PO_2$;
xxxi) $-P(O)(OH)_2$;
xxxii) $-SO_2NH_2$;
xxxiii) $-SO_2R^{30}$;
xxxiv) $-NO_2$;
xxxv) trihalomethyl having the formula: $-CF_3$, $-CCl_3$, $-CBr_3$;
xxxvi) and mixtures thereof;
wherein $R^{30}$ is hydrogen, $C_1$–$C_{20}$ linear or branched alkyl, $C_6$–$C_{20}$ aryl, $C_7$–$C_{20}$ alkylenearyl, or mixtures thereof; M is hydrogen, or a salt forming cation.

9. The compound of claim 7 wherein L has the formula:

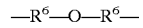

wherein one $R^6$ unit is $C_8$–$C_{30}$ hydroxy substituted linear alkylene unit and one $R^6$ unit is $C_1$–$C_{12}$ alkylene.

10. The compound of claim 9 wherein L is a glycidyl ether unit having the formula:

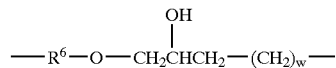

wherein w is from 1 to 27.

11. The compound of claim 7 wherein L is a glycidyl ether unit having the formula:

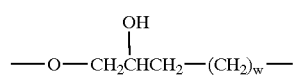

wherein w is from 1 to 27.

12. The compound of claim 7 wherein L has the formula:

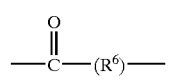

wherein $R^6$ is substituted with one or more $-COOR^{30}$ units.

13. The compound of claim 12 wherein L has the formula:

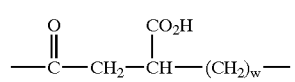

w is from 1 to 27.

14. The compound of claim 1 wherein $R^3$ is $C_2$–$C_6$ linear or branched alkylene; $R^4$ is hydrogen; j is 0; and k is from 3 to 50.

15. The compound of claim 14 wherein $R^3$ is a $C_2$–$C_4$ linear or branched alkylene.

16. The compound of claim 15 wherein k is from 5 to 30.

17. The compound of claim 16 wherein k is from 5 to 20.

18. The compound of claim 1 wherein $R^4$ is an anionic unit selected from the group consisting of:
   i) —$CO_2M$;
   ii) —$SO_2M$;
   iii) —$SO_3M$;
   iv) —$OSO_3M$;
   v) —$PO_2M$;
   vi) —$PO_3M$;
   vii) —$OPO_3M$;
   viii) and mixtures thereof;
   wherein M is hydrogen or a water soluble cation in a sufficient amount to provide charge neutrality.

19. The compound of claim 1 wherein n has an average value of from about 10 to about 3000.

20. The compound of claim 19 wherein n has an average value of from about 15 to about 1000.

21. A composition providing anti-wrinkle benefits to fabric, the composition comprising:
   a) from about 0.01% to about 99% by weight, of an anti-wrinkle agent having the formula:

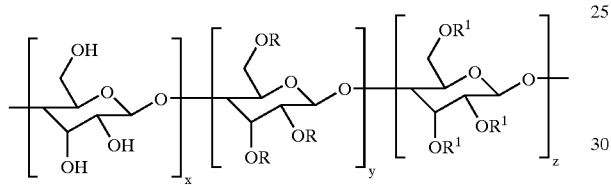

wherein each R unit is independently a siloxane unit having the formula:

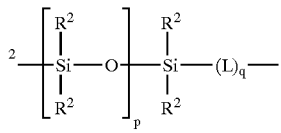

wherein each $R^2$ is independently a $C_1$–$C_{22}$ linear or branched, substituted or unsubstituted hydrocarbyl moiety; the index p is from 0 to about 50; L is a linking group; the index q is 0 or 1; and each $R^1$ unit is independently a fabric substantive unit having the formula:

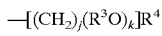

wherein $R^3$ is $C_2$–$C_{12}$ linear or branched alkylene; $R^4$ is hydrogen, an anionic unit, or mixtures thereof; the index j is from 0 to about 25; the index k is from 0 to about 50; and the sum of the indices x+y+z=n wherein n has an average value of from 5 to about 6000; and b) the balance carriers.

22. A laundry detergent composition comprising:
   a) from about 0.01% to about 30% by weight, of an anti-wrinkle agent having the formula:

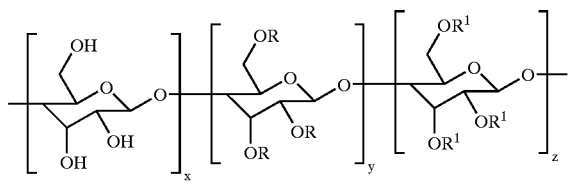

wherein each R unit is independently a siloxane unit having the formula:

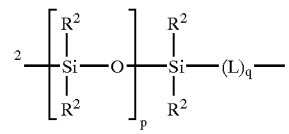

wherein each $R^2$ is independently a $C_1$–$C_{22}$ linear or branched, substituted or unsubstituted hydrocarbyl moiety; the index p is from 0 to about 50; L is a linking group; the index q is 0 or 1; and each $R^1$ unit is independently a fabric substantive unit having the formula:

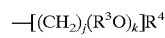

wherein each $R^3$ is independently $C_2$–$C_{12}$ linear or branched alkylene; $R^4$ is hydrogen, an anionic unit, and mixtures thereof; the index j is from 0 to about 25; the index k is from 0 to about 50; and the sum of the indices x+y+z=n wherein n has an average value of from 5 to about 6000;

b) from about 10% to about 80% by weight, of a surfactant system; and c) the balance carriers and other adjunct ingredients.

23. The composition of claim 22 wherein the surfactant system comprises:
   i) from about 0.01% by weight, of a surfactant selected from the group consisting of alkyl sulfate surfactants, alkoxy sulfate surfactants, mid-chain branched alkyl sulfate surfactants, mid-chain branched alkoxy sulfate surfactants, mid-chain branched aryl sulfonate surfactants, and mixtures thereof;
   ii) from about 0.01% by weight, of one or more aryl sulphonate anionic surfactants;
   iii) from about 0.01% by weight, of one or more nonionic surfactants.

* * * * *